United States Patent [19]

Pühler et al.

[11] Patent Number: 4,621,061
[45] Date of Patent: Nov. 4, 1986

[54] PLASMID P SG 2 AND PROCESS FOR ITS PREPARATION

[75] Inventors: Alfred Pühler; Wolfgang Wohlleben, both of Bielefeld; Michael Leineweber, Hofheim am Taunus, all of Fed. Rep. of Germany

[73] Assignee: Hoechst Aktiengesellschaft, Frankfurt, Fed. Rep. of Germany

[21] Appl. No.: 560,312

[22] Filed: Dec. 13, 1983

Related U.S. Application Data

[63] Continuation of Ser. No. 372,751, Apr. 28, 1982.

[30] Foreign Application Priority Data

Apr. 30, 1981 [DE] Fed. Rep. of Germany ....... 3117131

[51] Int. Cl.[4] .................. C12N 1/00; C12N 15/00
[52] U.S. Cl. .................. 435/320; 435/172.3; 935/29
[58] Field of Search .............. 435/317, 172.3, 91

[56] References Cited

U.S. PATENT DOCUMENTS 3,674,866  7/1972  Linder et al. ............... 435/101
4,273,875  6/1981  Mavis ...................... 435/91

OTHER PUBLICATIONS

Schrempf et al., J. Bacteriology, 121(2) (1975) 416.
Bibb et al., Molec. Gen. Genet. 154 (1977) 155.
Malik, J. Antibiotics 30(10) (1977) 897.
Yagisawa et al., J. Antibiotics 31(8) (1978) 809.
Huber et al., Can. J. Microbiol. 24 (1978) 631.
Malik et al., Plasmid 2 (1979) 627.
Omura et al., J. Antibiotics 32(10) (1979) 1058.
Nojiri et al., J. Antibiotics 33(1) (1980) 118.
Thompson et al., Nature 286 (1980) 525.
Hotta et al., J. Antibiotics 33(12) (1980) 1502.
Nakano et al., FEMS Microbiology Letters 9(1980) 111.
Omura et al., J. Antibiotics 34(4) (1981) 478.

*Primary Examiner*—Alvin E. Tanenholtz
*Attorney, Agent, or Firm*—Curtis, Morris & Safford

[57] ABSTRACT

The new streptomyces plasmid p SG 2, having a molecular weight of 9.2 megadaltons, a contour length of 4.58 μm and a molecular length of about 13.8 kilobases, is described, together with its preparation from a culture of "*Streptomyces ghanaensis*" ATCC 14 672.

3 Claims, 1 Drawing Figure

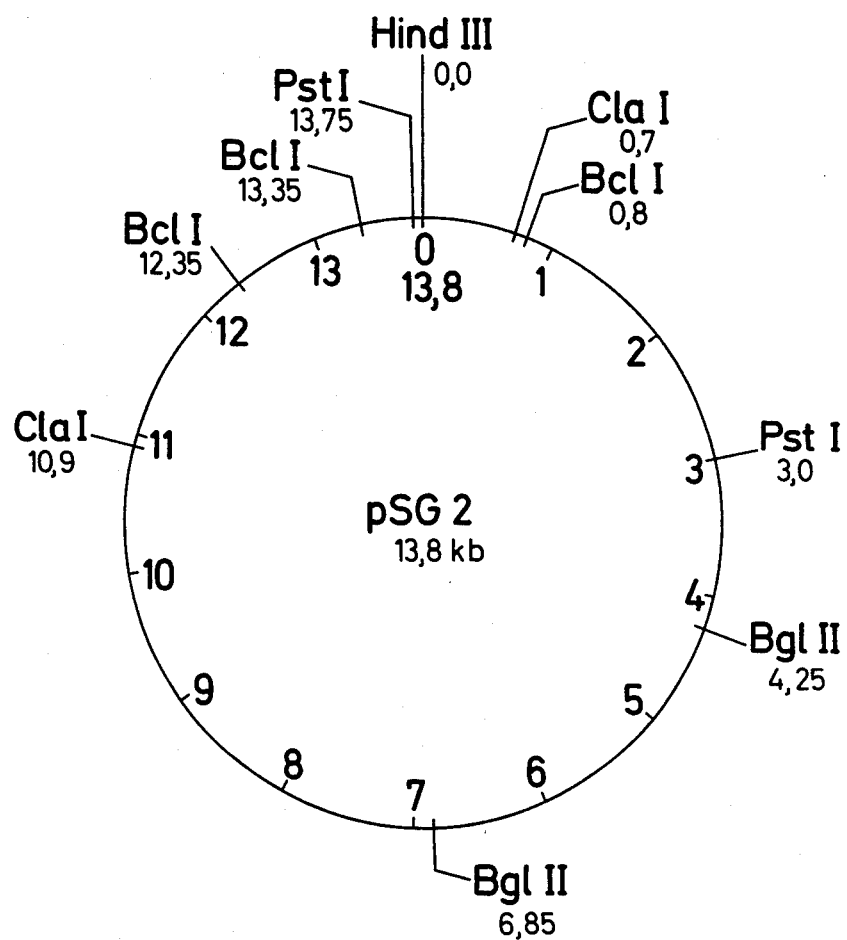

PLASMID P SG 2 AND PROCESS FOR ITS PREPARATION

This application is a continuation of application Ser. No. 372,751, filed Apr. 28, 1982.

The invention relates to the plasmid p SG 2 and a process for its preparation from a culture of *Streptomyces ghanaensis* ATCC 14 672.

It is known from German Offenlegungsschrift No. 3,005,226 (U.S. Pat. No. 4,273,857) that the plasmid p UC 6 can be prepared from a culture of *Streptomyces espinosus*. Furthermore, it is known from PCT application Ser. No. 01,169 that a plasmid which appears to be suitable as a vector for the introduction of DNA into microorganisms can be prepared from *Streptomyces lividans*.

It can be recognized from this that a particular importance is attributed to the application of genetic engineering methods to species of streptomyces which form antibiotics. However, the processes known hitherto have remained of little interest for practical application, because they have not proved satisfactory for the preparation of relatively large amounts of plasmid-DNA. For genetic engineering work, however, it is very important to have available adequate amounts of a plasmid if it is to be used as a vector for the preparation of genetically modified microorganisms.

The genetic improvement of the strains of streptomycetes used for the preparation of antibiotics, with the object of increasing the amount of the antibiotic formed, is an important task. However, it can only be carried out successfully, with genetic engineering methods, when a plasmid is available which is not immediately eliminated again from the species of streptomyces used as the host cell, as is frequently observed in the case of species not related to one another.

The object was therefore to prepare adequate amounts of a plasmid which is suitable as a vector for the genetic improvement of strains of streptomyces. It is obvious that this object can be achieved most easily when adequate amounts of plasmids have been found in another species of streptomyces.

It has now been shown that this object is achieved by the plasmid p SG 2, which is prepared from a culture of *Streptomyces ghanaensis* ATCC 14 672 and has a molecular weight of 9.2 megadaltons, a contour length of 4.58 μm and a molecular length of about 13.8 kilobases (=kb).

The strain of *Streptomyces ghanaensis* used here is described in detail in German Pat. No. 1,113,791 (U.S. Pat. No. 3,674,866) and is designated there as *S. ghanaensis* nov. sp. 4092. In a culture of *Streptomyces ghanaensis*, about 10 to 20 copies of the plasmid p SG 2 are present per cell. This plasmid is thus a suitable starting plasmid for the application of genetic engineering methods, both to the strain *Streptomyces ghanaensis* itself and to other species of streptomyces.

The plasmid p SG 2 has a molecular weight of about 9.2 megadaltons and a molecular length of approximately 13.8 kilobases. This information was obtained from agraose gel electrophoresis of the molecule itself and of its fragments. The length of 4.58±0.09 μm is determined from the measurement of 27 plasmid molecules by electron microscopy. The intensity of the plasmid band in the electrophoresis makes it possible to estimate the number of copies per cell at about 10 to 20. With fragmentation of the plasmid p SG 2 with a relatively large number of known restriction endonucleases, the cleavage sites and the fragment lengths were determined, and these are collated in the following table: Restriction characteristics of p SG 2 on digestion with various enzymes:

| Restriction enzyme | Number of cleavage sites | Length of the fragments | Total length |
|---|---|---|---|
| EcoRI | — | | |
| BamHI | — | | |
| SalI | — | | |
| HpaI | — | | |
| HindII | — | | |
| HindIII | 1 | ~14 kb | ~14 kb |
| BglII | 2 | 11.25 kb<br>2.6 kb | 13.85 kb |
| ClaI | 2 | 10.15 kb<br>3.65 kb | 13.8 kb |
| PstI | 2 | 10.85 kb<br>3.0 kb | 13.85 kb |
| BclI | 3 | 11.6 kb<br>1.25 kb<br>1.0 kb | 13.85 kb |

| Restriction enzyme | Number of cleavage sites | Length of the fragment | Total length |
|---|---|---|---|
| BstEII | 8 | 3.8 kb<br>2.45 kb<br>1.9 kb<br>1.15 kb<br>1.15 kb<br>1.0 kb<br>0.9 kb<br>0.8 kb | 13,65 kb |
| SmaI | 10 | not determined | |
| XhoI | 10 | | |
| Sau3A | 10 | | |

The attached drawing shows a restriction endonuclease fragmentation pattern of p SG 2. It shows one long and one short fragment each of PstI, ClaI and BglII and also one long and two short fragments of Bcl I. The relative position of the cleavage sites was determined by partial digestion and double digestion.

The plasmid p SG 2 is thus not attacked at all by the restriction endonucleases EcoR I, BamH I, Sal I, Hpa I and Hind II, but is cleaved by the restriction endonuclease Hind III into a fragment with a length of about 14 kb, by Cla I into two fragments with lengths of 10.15 and 3.65 kb, by Pst I into two fragments with lengths of 10.85 and 3.0 kb, by Bgl II into two fragments with lengths of 11.25 kb and 2.6 kb, and by Bcl I into three fragments with lengths of 11.6 kb, 1.25 kb and 1.0 kb.

This fragmentation pattern illustrates that the plasmid p SG 2 can be used for the construction of a vector plasmid. Work on the genetic modification of this plasmid can be carried out using the same processes as those which have successfully been used in the case of Escherichia coli plasmids and which are described, for example, by M. Bibb, J. C. Schottel and S. N. Cohen, Nature 284, 526–531 (1980), and C. J. Thompson, J. M. Ward and D. A. Hopwood, Nature 286, 525–527 (1980).

Antibiotic resistances can thus be introduced without difficulty into the Hind III, Cla I, Bgl II, Pst I and Bcl I cleavage sites. Furthermore, it appears to be possible to introduce, into the plasmid p SG 2, genes which lead to an increase in the antibiotic production in *Streptomyces ghanaensis*. Both genes for the biosynthetic process and also regulator genes are possible here. According to all observations made hitherto, p SG 2 plasmids modified in this way are just as capable of existence and reproduction in streptomyces cells as the starting plasmid.

The plasmid p SG 2 is obtained from a culture of *Streptomyces ghanaensis* ATCC 14 672 by growing the culture on a suitable medium, fragmenting the mycelium, incubating the fragmented mycelium, harvesting the culture and then lysing the mycelium. The isolation of the plasmid from the lysate is achieved by alkaline denaturation, in which an approximately 0.1–0.5 normal sodium hydroxide solution, to which about 1% of sodium dodecylsulfate has advantageously been added, is allowed to act on the lysate at about 0° C. for up to 10 minutes. The pH is then made weakly acid again by the addition of a buffer solution, thereby achieving renaturation. The mixture is then centrifuged and a pellet is produced from the supernatant by the addition of an excess of ethanol at −20° C. and subsequent centrifugation. This pellet is then taking up in a buffer solution and subjected to isopycnic density-gradient centrifugation in an ultracentrifuge, in a cesium chloride/ethidium bromide solution. The plasmids are then removed from the gradient by puncturing, purified by chromatography and characterised in an agarose gel and under an electron microscope. These are known methods (cf. R. Radloff, W. Bauer and J. Vinograd, Proc. Natl. Acad. Sci. USA, 57, 1,514–1,521 (1967), and A. A. Szalay, C. J. Mackey and H. W. R. Langridge, Enzyme Microb. Technol. 1, 154–164 (1976)).

EXAMPLE 1

The procedure for the preparation of the plasmid p SG 2 was as follows:

A culture of *Streptomyces ghanaensis* ATCC 14 672 was grown for 3 to 5 days, at 30° C., in 100 ml of a nutrient medium of the following composition:

| | |
|---|---|
| Glucose | 1 g |
| Peptone | 0.4 g |
| Yeast extract | 0.4 g |
| $MgSO_4.7H_2O$ | 0.05 g |
| $KH_2PO_4$ | 0.2 g |
| $K_2HPO_4$ | 0.4 g |
| Glycine | 2 g |
| Distilled water to | 100 g |

The culture supernatant was then poured off and the remainder of the culture was homogenized and then centrifuged for 5 minutes. After being washed twice in a buffer solution consisting of 10 millimolar Tris-HCl and 1 millimolar ethylenediaminetetraacetic acid (pH 7.5), to which 10% of sucrose had also been added, it was resuspended in 10 ml of a solution of the following composition:

50 millimoles of glucose
10 millimoles of EDTA
25 millimoles of Tris-HCl (=tris-(hydroxymethyl)-aminomethane hydrochloride)
2 mg/ml of lysozyme
This solution has a pH of 8.

After an incubation time of 30 to 60 minutes at 32° C., 20 ml of a freshly prepared 0.2 normal NaOH solution, which also contained 1% of sodium dodecyl-sulfate, were added and the mixture was left to stand at 0° C. for 5 minutes. After the addition of 15 ml of a 3 molar sodium acetate solution with a pH of 4.8, the ingredients were mixed again and incubated for 1 hour at 0° C. After further centrifugation, the supernatant was treated with 3 times its own volume of ethanol (96% strength) at −20° C. The precipitate was separated off by centrifugation, dried in vacuo and then taken up in 6 ml of a buffer of 10 millimoles of Tris-HCl and 1 millimole of EDTA (pH 7.5). The solution was then centrifuged in an ultracentrifuge for 2 days at 34,000 rpm in a cesium chloride/ethidium bromide gradient. The fraction containing the plasmids was then also chromatographed on apatite.

In this way, the plasmid p SG 2 was isolated in pure form.

EXAMPLE 2

The plasmid p SG 2 could also be prepared in the following way:

1 g of mycelium of *Streptomyces ghanaensis* ATCC 14 672 was grown for 3 to 5 days, at 30° C., in the same medium as described in Example 1. Here again, the culture supernatant was poured off and homogenized and the cell material was separated off by centrifugation. It was then washed twice with a buffer consisting of 10 millimoles of Tris-HCl and 140 millimoles of NaCl (pH 8.0). It was then resuspended in 5 ml of a buffer consisting of 100 millimoles of Tris-HCl, 20 millimoles of EDTA and 25% of sucrose. 0.1 ml of a lysozyme solution (30 mg/ml) was then added and the mixture was incubated for 20 minutes at 25° C. After cooling to 0° C. and the addition of 6 ml of ice-cold water, 1 ml of a 1% strength solution of sodium dodecyl-sulfate was added and, after the addition of a further 3.4 ml of a 5 molar NaCl solution, the ingredients were carefully mixed. The mixture was then left to stand at 4° C.

After the precipitation at 4° C. had ended, the mixture was centrifuged for 1 hour at 0° C. and 16,000 rpm. The supernatant was treated with a third of its own volume of a 42% strength polyethylene glycol solution (molecular weight of the polyethylene glycol: 6,000), a precipitate being formed. After precipitation at a temperature of 4° C. had ended, the plasmids were separated by centrifugation at 16,000 rpm for 15 minutes, and the pellet formed was then carefully taken up in 1 ml of a 0.4% strength solution of Sarcosyl* in a buffer consisting of 10 millimoles of Tris-HCl and 1 millimole of EDTA (pH 7.5). Using the same buffer, the volume was finally made up to 5 ml and the mixture was centrifuged in an ultracentrifuge, in a cesium chloride/ethidium bromide gradient. The subsequent procedure was as in Example 1. Hereinbefore all percentages are by weight, unless otherwise stated.

* (N-lauroyl-sarcoside)

We claim:

1. Plasmid pSG2 which is isolated from *Streptomyces ghanaensis* ATCC 14,672 and has a molecular weight of 9.2 megadaltons, a contour lenght of 4.58 μm and a molecular length of about 13.8 kilobases and which is not fragmented by the restriction endonucleases EcoR I, BamH I, Sal I, Hpa I and Hind III, but is cleaved by the restriction endonuclease Hind III into a fragment with a length of about 14 kb, by Cla I into two fragments with lengths of 10.15 and 3.65 kb, by Pst I into two fragments with lengths of 10.85 and 3.0 kb, by Bgl II into two fragments with lengths of 11.25 kb and 2.6 kb, and by Bcl I into three fragments with lengths of 11.6 kb, 1.25 kb and 1.0 kb.

2. A process for isolating the plasmid p SG 2 from a lysed culture of *Streptomyces ghanaensis* ATCC 14 672, which comprises denaturing the lysate with alkali, subsequently renaturing, and then precipitating the plasmid from the lysate with alcohol.

3. A process as claimed in claim 2, wherein the culture of *Streptomyces ghanaensis* is lysed, at a temperature of about 0° C., by means of a detergent in an amount of about 0.1% by weight.

* * * * *

UNITED STATES PATENT AND TRADEMARK OFFICE
CERTIFICATE OF CORRECTION

PATENT NO. : 4,621,061

DATED : November 4, 1986

INVENTOR(S) : Puhler et al.

It is certified that error appears in the above-identified patent and that said Letters Patent is hereby corrected as shown below:

Column 4, line 59 change "Hind III" to --Hind II--.

Signed and Sealed this

Twenty-fourth Day of March, 1987

Attest:

DONALD J. QUIGG

Attesting Officer

Commissioner of Patents and Trademarks